United States Patent [19]

Baier

[11] Patent Number: 4,585,399
[45] Date of Patent: Apr. 29, 1986

[54] HOSE PUMP

[75] Inventor: Manfred Baier, Bretten-Diedelsheim, Fed. Rep. of Germany

[73] Assignee: Richard Wolf GmbH, Fed. Rep. of Germany

[21] Appl. No.: 743,828

[22] Filed: Jun. 12, 1985

[30] Foreign Application Priority Data

Jun. 19, 1984 [DE] Fed. Rep. of Germany ... 8418491[U]

[51] Int. Cl.$^4$ .............................................. F04B 43/12
[52] U.S. Cl. .................................................... 417/477
[58] Field of Search ................ 417/477, 476, 474, 475

[56] References Cited

U.S. PATENT DOCUMENTS

| 3,138,111 | 6/1964 | Kling et al. | 417/477 X |
| 3,502,034 | 3/1970 | Pickup | 417/475 |
| 3,756,752 | 9/1973 | Stenner | 417/477 |
| 4,515,535 | 5/1985 | D'Silva | 417/477 |

Primary Examiner—Richard E. Gluck
Attorney, Agent, or Firm—Hill, Van Santen, Steadman & Simpson

[57] ABSTRACT

The hose pump in particular for drawing flushing liquids out of bodily cavities, is so constructed that the extremities of the hose which is to be inserted into the pump housing have different coupling or plug elements for suction and pressure hoses which are to be connected, and different fitting elements for complementary fitting elements of the pump housing or of the coupling element, whereby the positions of the two extremities in the housing cannot be transposed and accidental reversal of the suction and pressure hoses is prevented.

2 Claims, 1 Drawing Figure

U.S. Patent  Apr. 29, 1986  4,585,399
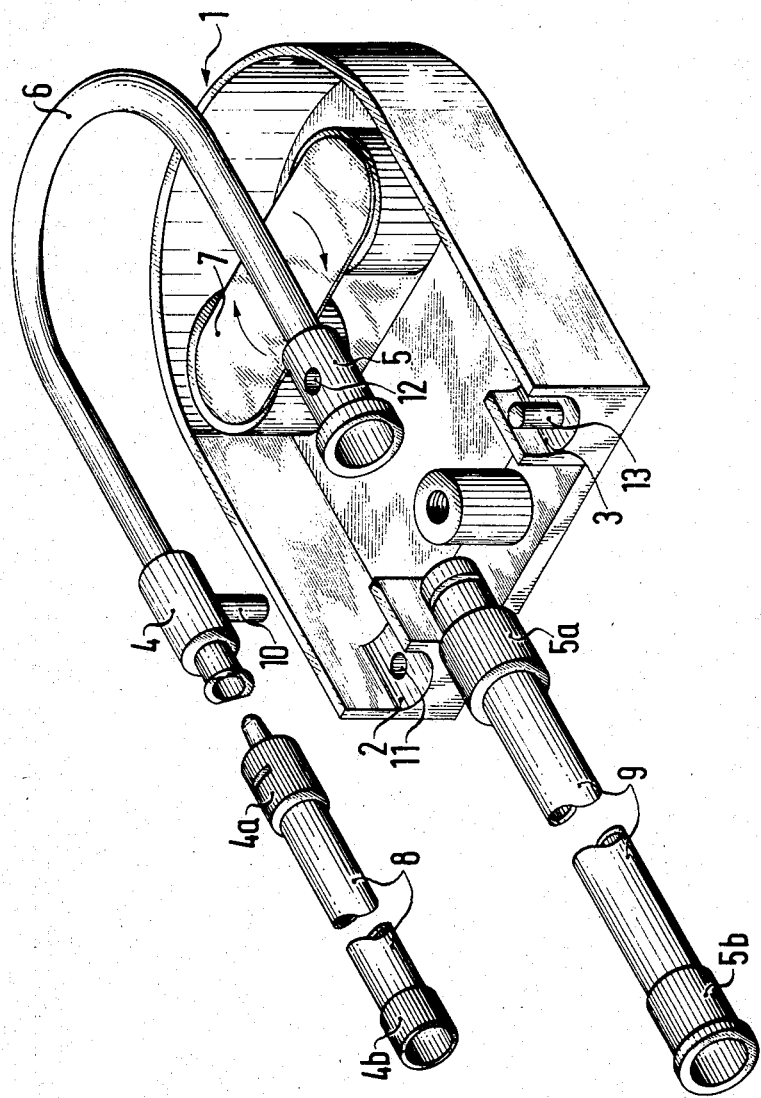

HOSE PUMP

BACKGROUND OF THE INVENTION

Field of the Invention

The invention relates to a peristaltic or hose pump, and in particular to a pump for drawing flushing liquids and stone or tissue particles out of bodily cavities.

The pump hoses of such hose pumps are easy to cleanse and disinfect or are replaced by new hoses, exactly like the connecting hoses.

During the cleansing and disinfecting operations, the connecting hoses have to be released from the pump hose and reconnected thereafter, so that if operating instructions are disregarded, it is possible to confuse the connectors and to perform a wrong insertion into the pump housing, which represents a considerably danger to the patients. This risk also prevails when soiled hoses are being replaced by new hoses.

SUMMARY OF THE INVENTION

The object of the invention consists in assuring in the case of hose pumps of the kind referred to in the foregoing, that the pump hose may be inserted into the pump housing only with the suction and pressure sides in the correct positions, and that the coupling hoses may be connected to the suction and pressure sides of the pump hose in the correct manner, only. In accordance with the invention, this problem is resolved in that the two extremities of the hose which is to be placed in the pump housing comprise different coupling and plug elements for suction and pressure hoses which are to be connected and different projections or plug configurations which fit into complementary recesses of the pump housing or of the plug elements. Thanks to this solution, an erroneous insertion of the pump hose into the pump housing cannot occur in any case, and the coupling hoses may moreover be joined to the suction and pressure sides of the pump hose in the correct position only.

DETAILED DESCRIPTION OF THE PREFERRED EMBODIMENT

A specific embodiment of the invention is described in the following with reference to the drawing, in which an example of a hose pump in accordance with the invention is illustrated together with coupling hoses, in perspective and with its parts disassembled.

The pump housing 1 of the hose pump comprises two reception seats 2 and 3 for the two coupling extremities or connectors 4 and 5 of a flexible pump hose 6 which is to be inserted into the housing 1, and which operates in conjunction with a revolving pumping roller 7 by means of which fluid is forced through the hose. The two coupling elements 4 and 5 are differently formed, so that the coupling element or inlet connector 4 may be coupled only to a coupling element 4a of a suction hose 8, and the coupling element or outlet connector 5 may be coupled only to a coupling element 5a of a pressure-side hose 9, thereby preventing erroneous connections.

So that an erroneous interchange between the coupling extremities 4 and 5 may complementarily also be made impossible in the reception seats 2 and 3 of the pump housing 1, the coupling element 4 is provided with a projection 10 for engagement in a recess bore 11 of the inlet seat 2, and the coupling element 5 is provided with a bore 12 for engagement of a pin 13 of the outlet seat 3. This provides the assurance that an erroneous insertion of the pump hose 6 into the pump housing 1, as well as that an erroneous connection of the suction and pressure-side hoses 8 and 9 to the coupling extremities 4 and 5 of the pump hose 6, cannot occur. The suction side of the hose pump is moreover connected via the hose 8 and a receiving vessel to an instrument which is to be introduced into a bodily cavity, these connecting elements also being co-ordinated with each other in a fool-proof and unmistakable manner by appropriately formed coupling and plug configurations.

Although the invention has been described in relation to a pump for drawing flushing liquids and the like from bodily cavities, it will be understood that the invention is equally applicable to hose pumps used in other fields.

What is claimed is:

1. In a hose pump for drawing fluids from a body cavity, said pump having a hose having an inlet connector at one end for coupling to a suction hose and an outlet connector at the other end for coupling to a pressure hose, said inlet and outlet connectors being different to prevent inadvertent connection of the outlet connector with a hose other than the pressure hose, a housing for receiving the hose with the inlet connector being in an inlet seat and the outlet connector being in an outlet seat, and means for forcing a fluid through said hose inserted in said housing, the improvements comprising said housing and inlet and outlet connectors having cooperating means to prevent transposition of said inlet and outlet connectors in said housing, said means including one of said inlet and outlet seats having a bore for receiving a pin of the connector associated therewith, the other of said inlet and outlet seats having a pin for insertion in a bore in the connector associated therewith so that the connector associated with the one seat cannot be placed in the other seat.

2. In a hose pump according to claim 1, wherein said one seat is the inlet seat receiving a pin carried by the inlet connector and the other seat is the outlet seat having a pin received in a bore of the outlet connector.

* * * * *